United States Patent
Mitterer et al.

(10) Patent No.: US 8,388,847 B2
(45) Date of Patent: Mar. 5, 2013

(54) METHODS OF CONCENTRATING SHEAR-SENSITIVE BIOPOLYMERS

(75) Inventors: Artur Mitterer, Orth/Donau (AT); Meinhard Hasslacher, Vienna (AT); Christa Mayer, Wolfsthal (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 178 days.

(21) Appl. No.: 12/549,247

(22) Filed: Aug. 27, 2009

(65) Prior Publication Data

US 2010/0051550 A1    Mar. 4, 2010

Related U.S. Application Data

(60) Provisional application No. 61/190,453, filed on Aug. 28, 2008.

(51) Int. Cl.
    *B01D 11/00* (2006.01)
    *B01D 61/00* (2006.01)
    *C02F 1/44* (2006.01)
    *C12N 7/04* (2006.01)

(52) U.S. Cl. ............ 210/645; 210/651; 210/321.71; 435/236; 530/383

(58) Field of Classification Search ......... 210/645, 210/651, 500.29, 500.41, 637, 635; 435/193, 435/236; 530/383
See application file for complete search history.

(56) References Cited

U.S. PATENT DOCUMENTS

| | | | |
|---|---|---|---|
| 5,211,850 A | | 5/1993 | Shettigar et al. |
| 6,313,285 B1 * | | 11/2001 | Butler et al. ............ 536/25.4 |
| 6,596,172 B1 * | | 7/2003 | Kopf ........................ 210/635 |
| 6,797,169 B1 * | | 9/2004 | Ide et al. .................. 210/500.27 |
| 6,967,239 B1 * | | 11/2005 | Chtourou et al. ............ 530/383 |
| 7,094,348 B2 * | | 8/2006 | Sunohara et al. ......... 210/321.88 |
| 2009/0188862 A1 * | | 7/2009 | Nikolic et al. ............... 210/637 |
| 2010/0314317 A1 * | | 12/2010 | Nikolic et al. ............... 210/637 |
| 2010/0317081 A1 * | | 12/2010 | Nikolic et al. ............... 435/193 |

FOREIGN PATENT DOCUMENTS

| | | |
|---|---|---|
| EP | 2092974 | 8/2009 |
| JP | 05168705 | 7/1993 |
| WO | WO-97/48483 | 12/1997 |
| WO | WO-2009/086296 | 7/2009 |

OTHER PUBLICATIONS

International Search Report and Written Opinion of the International Searching Authority, European Patent Office, PCT/US2009/055227, dated Dec. 4, 2009.

* cited by examiner

*Primary Examiner* — Ana Fortuna

(74) *Attorney, Agent, or Firm* — Marshall, Gerstein & Borun LLP

(57) ABSTRACT

The invention relates generally to methods of concentrating mixtures including shear sensitive biopolymers, such as von Willebrand Factor. Conventional methods of concentrating biopolymers impart too much shear stress, which causes the degradation of shear sensitive biopolymers. The methods disclosed herein reduce the shear stress while maintaining a high rate of filtrate flux. Disclosed herein is a method for concentrating shear sensitive biopolymers including flowing a mixture with a shear sensitive biopolymer into a hollow fiber dialysis module to form a retentate having a shear sensitive biopolymer concentration that is greater than that of the mixture. Hollow fiber dialysis modules have high filtrate fluxes and low shear rates at low flow rates. This ensures a high product yield and minimal loss of shear sensitive biopolymers.

13 Claims, 4 Drawing Sheets

METHODS OF CONCENTRATING SHEAR-SENSITIVE BIOPOLYMERS

CROSS-REFERENCE TO RELATED APPLICATION

The benefit under 35 U.S.C. §119(e) of U.S. Provisional Patent Application Ser. No. 61/190,453 filed Aug. 28, 2008, the disclosure of which is incorporated herein by reference, is hereby claimed.

BACKGROUND OF THE INVENTION

1. Field of the Disclosure

The disclosure generally relates to methods of concentrating shear sensitive biopolymers, such as von Willebrand factor (vWF).

2. Brief Description of Related Technology

Known methods of concentrating (and diafiltrating) biopolymers include tangential flow (cross flow) ultrafiltration (and diafiltration) in flat plate and hollow fiber devices. These devices operate at flow rates and transmembrane pressures sufficiently high to ensure a filtrate flux suitable for cost-effective operation. However, these operating conditions create high shear rates. Additionally, these devices may include screens to further increase filtrate flux. These screens also increase the shear stress imparted to biopolymers. Such shear stress is particularly undesirable when attempting to concentrate shear sensitive biopolymers, such as proteins or viral particles, because the stresses can destroy, denature, or inactivate the biopolymer.

There are various known methods to reduce shear stress during concentration and/or diafiltration in flat plate or tangential flow (cross flow) hollow fiber devices. Those methods include reducing the flow rate, increasing the membrane surface area, and increasing the cut-off size of the membrane. However, each of these methods has various problems. For example, reducing the flow rate also reduces the filtrate flux, which undesirably increases the total operation time, increases the risk of membrane fouling, and increases the amount of time the shear sensitive biopolymer is exposed to the shear stress. Increasing the membrane surface area at low flow rates keeps the filtrate flux high and prevents an increase in total operation time. However, at reduced flow rates, the risk of membrane fouling increases. The increased membrane surface area causes more product loss due to increased surface adsorption, costs more for increased membrane area and buffer consumption, and may have a dead volume larger than the desired volume of the product after concentration. Increasing the cut-off size of the membrane results in sufficient filtrate flux due to the larger pore size. However, problems of increased membrane fouling or incompatibility with the shear sensitive biopolymer (i.e., the biopolymer may pass through the membrane and be lost in the filtrate) remain.

Detergents are used in many bio-processing operations to avoid surface adsorption and aggregate formation of proteins. These operations, however, can require specialized buffer additives to stabilize shear sensitive biopolymers.

For tangential flow hollow fiber devices, the recommended shear rate is 2000 to 8000 $sec^{-1}$ and 2000 to 4000 $sec^{-1}$ for shear sensitive feed stock. See GE Healthcare, Operating Handbook: Hollow fiber cartridges for membrane separations 8 (2004). However, shear sensitive biopolymers, such as, for example, vWF or viral particles, begin to degrade, denature, or unfold at shear rates above 2000 $sec^{-1}$. Therefore, there is a need in the art for methods of concentrating shear sensitive biopolymers without imparting high levels of shear stress.

Generally, the prior art does not sufficiently teach or suggest to one of ordinary skill in the art a cost-effective method of concentrating shear sensitive biopolymers without substantial loss of the biopolymer to protein precipitation, membrane fouling, and membrane surface adsorption. Similarly, reducing the flow rate of the biopolymer-containing mixture to thereby reduce the shear stress in devices does not provide an effective alternative because a certain minimum flow rate is needed to avoid membrane fouling and precipitate adsorption.

SUMMARY OF THE INVENTION

Disclosed herein is a method of concentrating shear sensitive biopolymers that includes flowing a mixture containing a shear sensitive biopolymer, such as vWF, into a hollow fiber dialysis module to form a retentate having a shear sensitive biopolymer concentration that is greater than that of the mixture. The method can further include buffer exchange, or dialysis, with the mixture containing a shear sensitive biopolymer during or after concentration.

The membranes of the hollow fiber dialysis modules preferably have a thickness of less than about 200 micrometers, for example, the membranes may be about 10 micrometers to about 100 micrometers thick, and preferably are about 30 micrometers thick. In preferred embodiments, the wall shear rates in the hollow fiber dialysis modules are less than about 2300 $sec^{-1}$, and preferably about 50 $sec^{-1}$ to about 1800 $sec^{-1}$. The transmembrane pressure in the hollow fiber dialysis module preferably is about 1 mmHg to about 600 mmHg (about 0.1 kPa to about 80 kPa), and more preferably about 10 mmHg to about 150 mmHg (about 1 kPa to about 20 kPa).

The mixture containing the shear sensitive biopolymer can optionally contain a solution buffer. If the mixture includes a solution buffer, the method can further include displacing a portion of the solution buffer with a dialysis buffer.

In preferred embodiments, the retentate includes at least about 70% of the shear sensitive biopolymer in the mixture, preferably at least about 80% of the shear sensitive biopolymer in the mixture, and more preferably at least about 90% of the shear sensitive biopolymer in the mixture. The retentate preferably retains at least about 70% of the activity of the shear sensitive biopolymer in the mixture, and more preferably it retains at least about 80% of the activity of the shear sensitive biopolymer in the mixture.

The disclosed method provides a cost-effective process to concentrate shear sensitive biopolymers while avoiding substantial loss of the biopolymer to protein precipitation, membrane fouling, and membrane surface adhesion.

Additional features of the invention may become apparent to those skilled in the art from a review of the following detailed description, taken in conjunction with the drawings, the examples, and the appended claims.

BRIEF DESCRIPTION OF THE DRAWING FIGURES

For a more complete understanding of the disclosure, reference should be made to the following detailed description and accompanying drawing wherein.

Figure 1:
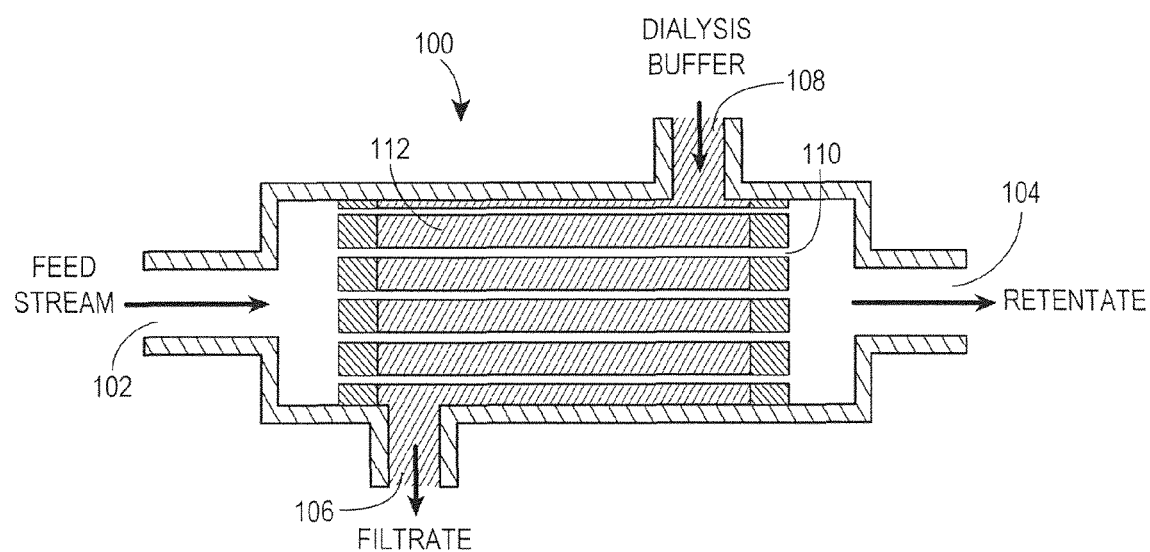
FIG. 1 is a cross-sectional view of a hollow fiber dialysis module (not to scale)

While the disclosed method for concentrating shear sensitive biopolymers is susceptible of embodiments in various forms, there are illustrated in the drawings (and will hereafter be described) specific embodiments of the invention, with the understanding that the disclosure is intended to be illustrative, and is not intended to limit the invention to the specific embodiments described and illustrated herein.

DETAILED DESCRIPTION OF THE INVENTION

The invention relates generally to methods of concentrating shear sensitive biopolymers from a mixture containing the same. Known methods of concentrating biopolymers would impart undesirably high shear stress that would destroy, denature, or inactivate shear sensitive biopolymers. Disclosed herein is a method of concentrating shear sensitive biopolymers that includes flowing a mixture containing a shear sensitive biopolymer into a hollow fiber dialysis module to form a retentate having a shear sensitive biopolymer concentration that is greater than that of the mixture. The disclosed method ensures a shear stress sufficiently low to avoid destruction of the shear sensitive biopolymers, while maintaining a high filtrate flux.

Shear sensitive biopolymers that are suitable for concentration according to the disclosed method include those that are susceptible to damage, destruction, and/or loss of activity when exposed to significant shear forces (i.e., relatively large velocity gradients). An example of such a shear sensitive biopolymer is the von Willebrand factor (vWF), which circulates in plasma complexed with factor VIII and assists in the regulation of biological blood coagulation activity. While vWF exists in plasma in a series of oligomeric/polymeric forms having molecular weights ranging from about 1,000 kDa (kilodalton) to about 20,000 kDa based on 520-kDa dimers, the disclosed method is not necessarily limited in its ability to concentrate shear sensitive biopolymers based only on this particular molecular weight range.

Specifically, vWF is sensitive to shear forces induced by the velocity gradient of a transporting fluid medium, in particular when vWF passes through or near a filter membrane (i.e., where flow constrictions and circuitous flow paths in the neighborhood of filter membrane pores result in particularly large velocity gradients). For example, shear rates above 2000 sec$^{-1}$ (inverse seconds) cause vWF to transform from a globular molecule to an extended chain molecule. This structural transformation increases the likelihood of adhesion to filter surfaces and other proteins. Large multimers of vWF are particularly susceptible to this structural transformation and an increased likelihood of adhesion. During concentration, increased adhesion decreases product yield, and the loss of large multimers decreases the vWF Ristocetin cofactor activity.

Hollow fiber dialysis modules have high filtrate fluxes and low shear rates. These modules can ensure a high product yield and minimal loss of shear sensitive biopolymers. Hollow fiber dialysis modules are devices with hollow fibers, or tubular membranes, spanning the length of the device, as illustrated in FIG. 1 (not to scale). Hollow fiber dialysis modules are known for use in blood dialysis and are commercially available from, for example, Edwards Lifesciences (Saint-Prex, Switzerland) and Asahi Kasei Chemicals Corp. (Tokyo, Japan). While not wishing to be bound to any particular theory, it is believed that the modules operate on the principle of dialysis, in which pressure gradients are not the main driving force for mass transfer. Instead, concentration gradients drive mass transfer, or buffer exchange, across the membrane.

Shown in FIG. 1 is a hollow fiber dialysis module 100 having a feed stream inlet 102, a retentate stream outlet 104, a filtrate stream outlet 106, and an optional dialysis buffer stream inlet 108. The hollow fiber dialysis module 100 has hollow fibers 110 that span the module 100 parallel to feed flow. The hollow fibers 110 are surrounded by a potting material 112. The hollow fiber dialysis modules can be used singly or in series or parallel depending upon feed volume.

High filtrate fluxes in hollow fiber dialysis modules are attainable because the hollow fiber dialysis module membrane is much thinner than membranes in ultrafiltration and tangential flow hollow fiber devices. The latter membranes are more than 200 micrometers thick because these membranes must withstand high transmembrane pressures, large volumes (because of recirculation), and multiple uses. Membranes that thick reduce filtrate flux. In contrast, the membranes of hollow fiber dialysis modules are less than about 200 micrometers thick, preferably about 10 micrometers to about 100 micrometers thick, and more preferably about 30 micrometers thick. The thin membrane allows a higher filtrate flux and, therefore, the transmembrane pressure can be lower than other modules.

Because the hollow fiber dialysis module has a high filtrate flux, fewer passes through the hollow fiber dialysis module are required than required in tangential flow hollow fiber devices. Furthermore, when the dialysis buffer flows in concurrent or counter-current flow, the number of recirculations can be reduced compared to processes where the dialysis buffer is added directly to the feed stream. The efficiency of the hollow fiber dialysis modules is far greater than efficiencies possible in ultrafiltration and tangential flow hollow fiber devices, which require many more recirculations to achieve the same concentration. Fewer passes at low shear rates through hollow fiber dialysis modules enable more of the protein to retain its structure compared to many passes at high shear rates, as found in ultrafiltration or tangential flow hollow fiber devices.

The shear rates in the hollow fiber dialysis module are preferably below about 2300 sec$^{-1}$. The flow rate of the shear sensitive biopolymer-containing mixture can be adjusted or controlled to ensure shear rates below certain levels, for example, below 2300 sec$^{-1}$, below 2000 sec$^{-1}$, or below 1800 sec$^{-1}$. Shear rate is calculated by the following equation:

$$\text{Shear rate} = \frac{4*Q}{n(\pi*r^3)},$$

wherein Q is the flow rate (mL/sec), n is the number of fibers in the hollow fiber dialysis module, and r is the inner radius of a fiber (cm).

See Table 1 for shear rates at various flow rates and number of fibers for modules with a 0.2 millimeter fiber inner diameter.

TABLE 1

Shear rates at various flow rates for modules with varying fiber counts

| Flow (mL/min) | Module with 4775 fibers | Module with 7925 fibers | Module with 11141 fibers | Module with 12547 fibers |
| --- | --- | --- | --- | --- |
| | Wall shear rate (sec$^{-1}$) | | | |
| 50 | 222 | 134 | 95 | 85 |
| 100 | 444 | 268 | 190 | 169 |
| 200 | 889 | 536 | 381 | 338 |

TABLE 1-continued

Shear rates at various flow rates
for modules with varying fiber counts

| Flow (mL/min) | Module with 4775 fibers | Module with 7925 fibers | Module with 11141 fibers | Module with 12547 fibers |
|---|---|---|---|---|
| | Wall shear rate (sec$^{-1}$) | | | |
| 300 | 1333 | 803 | 571 | 507 |
| 400 | 1778 | 1071 | 762 | 676 |
| 500 | 2222 | 1339 | 952 | 846 |

Preferably, the transmembrane pressure in the hollow fiber dialysis module is about 1 mmHg (millimeters mercury) to a maximum of about 600 mmHg (about 0.1 kPa (kilopascal) to about 80 kPa), and more preferably about 10 mmHg to about 150 mmHg (about 1 kPa to about 20 kPa). Ultrafiltration and tangential flow hollow fiber devices can withstand much higher pressures because they have thick membranes. These devices also require higher pressures to ensure efficiency and a minimum filtrate flow for economical operations. For example, maximum transmembrane pressures for tangential flow hollow fiber devices are around 2600 mmHg to 3100 mmHg (340 kPa to 415 kPa) at 10° C. At room temperature, the maximum transmembrane pressures are about 2300 mmHg to 2600 mmHg (310 kPa to 345 kPa). See GE Healthcare, Operating Handbook: Hollow fiber cartridges for membrane separations 19 (2004). These pressures and flow rates, however, are likely to destroy shear sensitive biopolymers, such as vWF.

The membranes of the hollow fiber dialysis modules can be made from various materials that tend to resist the adhesion of biopolymers. Typically, very hydrophilic membranes, or low protein binding membranes, are preferred. Preferred materials have a protein adsorption of below 1 g/m$^2$ (gram per square meter). Some suitable materials include, for example, cellulose derivatives (e.g., modified or regenerated cellulose) and synthetic membranes (e.g., polysulfone, polyethersulfone, polyvinylidene fluoride, polyacrylonitrile, polyimide, ceramic, and aliphatic polyamide). Preferred membrane materials include polysulfone, polyethersulfone, and modified cellulose. For example, typical protein adsorption is 0.5 g/m$^2$ for polyethersulfone and 0.1 g/m$^2$ for regenerated cellulose.

The hollow fiber dialysis modules can operate in various modes including concentration, concentration and diafiltration, and concentration and dialysis. In concentration, with continued reference to FIG. 1, a feed stream flows into the inlet 102 through the hollow fibers 110 to form a retentate that exits the module 100 through the outlet 104. Small molecules from the mixture containing the shear sensitive biopolymers pass through the membrane of the hollow fibers 110 into the potting material 100, and are removed from the module 100 through the outlet 106 as filtrate. The shear sensitive biopolymers travel along the hollow fibers 110 to form the retentate.

The mixture containing the shear sensitive biopolymers can include a solution buffer. For example, a solution buffer for shear sensitive biopolymers, such as vWF, can be a 20 mM (millimolar) HEPES and 150 mM NaCl buffer, with a pH of 7.4 at room temperature. HEPES, or 4-(2-hydroxyethyl)-1-piperazineethanesulfonic acid, is a zwitterionic organic chemical buffering agent. The solution buffer can pass through the membrane of the hollow fibers 110 into the potting material and exit the hollow fiber dialysis module as filtrate.

Figure 2:
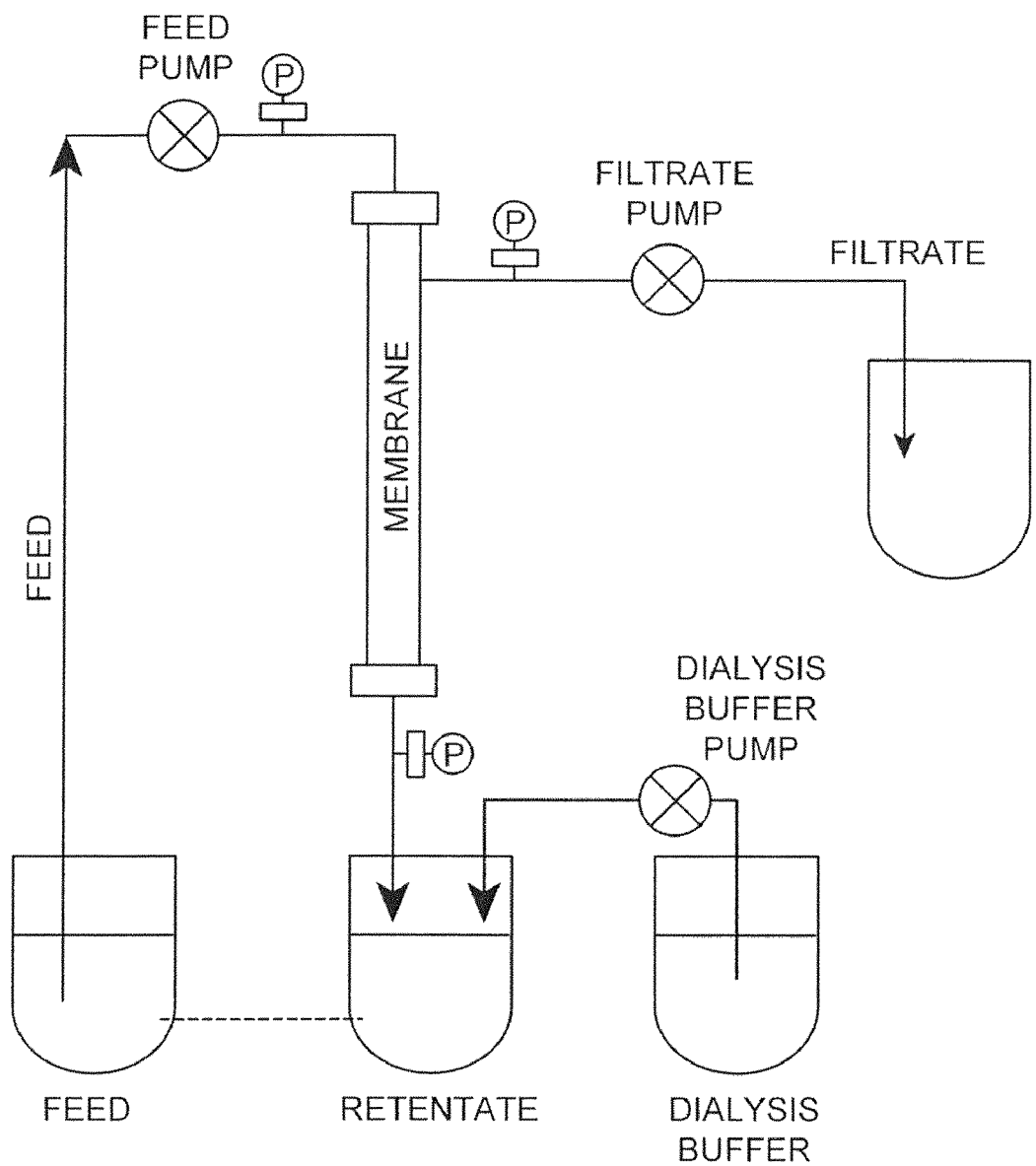
FIG. 2 is a process flow diagram of a hollow fiber dialysis module with the dialysis buffer being added directly to the retentate.

The retentate will include the shear sensitive biopolymers. The retentate can optionally include a dialysis buffer. For example, a dialysis buffer for shear sensitive biopolymers, such as vWF, can be a 20 mM citrate and 15 mM glycine buffer, with a pH of 7.3 at room temperature. In diafiltration, the dialysis buffer can be added directly to the retentate during or after concentration, as illustrated in FIG. 2. FIG. 2 is a process flow diagram of a hollow fiber dialysis module with the dialysis buffer being added directly to the retentate. The retentate can optionally be returned to the feed if multiple passes through the hollow fiber dialysis module are desired, as shown by the dotted line.

Figure 3:
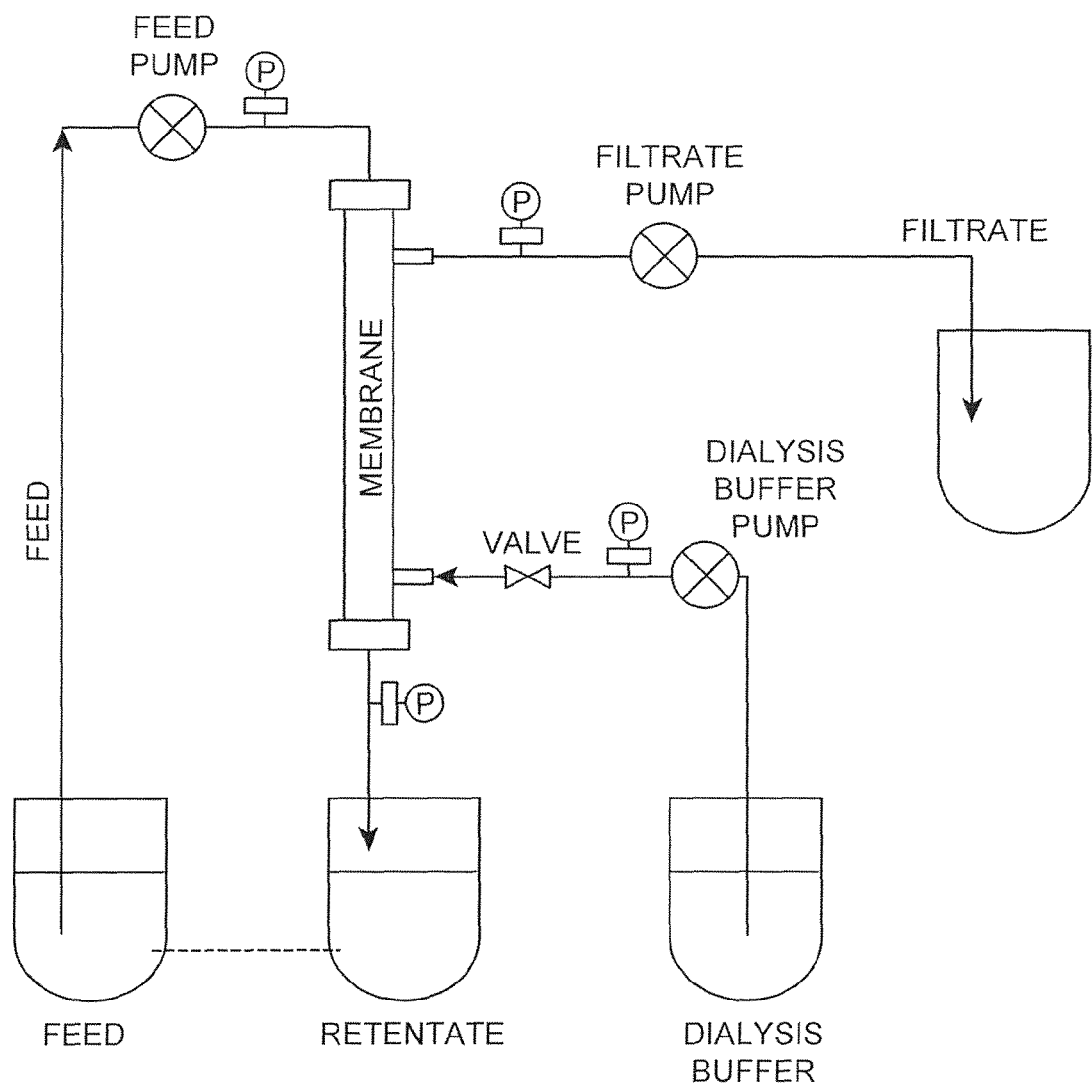
FIG. 3 is a process flow diagram of a hollow fiber dialysis module with the dialysis buffer introduced counter-current to the feed flow; and, FIG. 4 is a chart showing process data for Experiment 2-1.

In dialysis, the dialysis buffer can flow through the potting material 112 during or after concentration, as illustrated in FIG. 1, in either concurrent flow or counter-current flow, displacing the solution buffer. FIG. 3 is a process flow diagram of a hollow fiber dialysis module with the dialysis buffer introduced counter-current to the feed flow. Concurrent flow (not shown) can be achieved by switching the filtrate and dialysis buffer streams. The retentate can optionally be returned to the feed if multiple passes through the hollow fiber dialysis module are required, as shown by the dotted line.

As illustrated in FIG. 1, the dialysis buffer enters the module 100 through the inlet 108 and contacts outer surfaces of the membrane of the hollow fibers 110 in counter-current flow, and displaces a portion of the solution buffer. Specifically, in FIG. 1, a feed stream containing a solution buffer and shear sensitive biopolymer enters a module 100 through the inlet 102. A dialysis buffer enters the module through inlet 108, and flows through a potting material 100 in counter-current flow. In hollow fibers 110, a portion of the solution buffer and a portion of the dialysis buffer pass through the membrane. The solution buffer is removed as filtrate, and the dialysis buffer and the shear sensitive biopolymers form a retentate that exits the module 100 through the outlet 104. Alternatively, the dialysis buffer and filtrate streams can be switched to run the dialysis buffer in concurrent flow with the feed stream (not shown).

In flat plate and tangential flow hollow fiber ultrafiltration devices, dialysis is not performed by buffer exchange through the membrane. Instead, after concentration, dialysis buffer is added to the retentate and concentrated again. This is performed many times to achieve sufficient buffer exchange. In contrast, the hollow fiber dialysis modules can operate in concentration and dialysis mode simultaneously, reducing the number of passes through the module.

The buffers preferably are compatible with biopolymers. The buffers will generally vary based on the specific requirements for specific biopolymers. For most therapeutic proteins, for example, the buffers preferably have a pH of about 4 to about 9 at room temperature. Buffers outside this pH range may cause denaturation of the protein. However, some proteins (e.g., pepsin) function best in acidic environments, for example, in a pH of about 1 to about 2. Further, the buffers preferably should not contain reducing or chaotropic compounds that would destroy the biopolymer. Reducing agents are only harmful for proteins or peptides that include disulfide bonds. Most therapeutic proteins include disulfide bonds and reducing agents can destroy these bonds. Reducing components include, for example, beta-mercaptoethanol, mercaptoethylamine, dithiothreitol, and tris(2-carboxyethyl)phosphine. Chaotropic components include, for example, urea, guanidinium chloride, guanidine thiocyanate, and kalium thiocyanate.

After concentration, the retentate preferably includes at least about 70% of the shear sensitive biopolymer present in the mixture, and more preferably at least about 80%, and even more preferably at least about 90% of the shear sensitive biopolymer present in the mixture. After concentration, the shear sensitive biopolymer present in the retentate preferably retains at least about 70% of the activity present in the mixture, and more preferably at least about 80% of the activity present in the mixture.

The disclosed method avoids the use of detergents to reduce surface adsorption and aggregate formation and the development of specialized buffer additives to stabilize shear sensitive biopolymers. The use of detergents is problematic because, above critical concentrations, they can form high molecular weight micelles that behave like proteins and could be concentrated along with the shear sensitive biopolymers. Therefore, the final concentration of detergent would be difficult to control.

EXAMPLES

The following examples are provided to illustrate the invention, but are not intended to limit the scope thereof. Example 1 describes four experiments performed with a hollow fiber dialysis module with a 3000 cm$^2$ membrane surface area. Example 2 describes two experiments performed with a hollow fiber dialysis module with a 7000 cm$^2$ membrane surface area. The membrane surface area is the inner membrane surface area in one hollow fiber multiplied by the number of hollow fibers in the module. These experiments were performed with the dialysis buffer flowing in counter-current flow, as illustrated in FIG. 2.

Example 1

Four experiments were performed with vWF as the shear sensitive biopolymer with a hollow fiber dialysis module. The hollow fiber dialysis module had a 3000 cm$^2$ membrane surface area, a 30 micrometer thick membrane, a fiber length of 100 millimeters, and a fiber inner diameter of 200 micrometers. The membrane material was polyethersulfone. The concentrations of the feed streams were 0.7 grams of vWF protein per liter (g vWF/L), 0.56 g vWF/L, 0.39 g vWF/L, and 0.27 g vWF/L. The concentrations of the retentate, after concentration, were 2.52 g vWF/L, 4.59 g vWF/L, 2.23 g vWF/L, and 1.26 g vWF/L, respectively. The experiments took approximately 2 to 4 hours to complete.

The solution buffer, in the feed stream, was a 20 mM (millimolar) HEPES and 150 mM NaCl buffer, with a pH of 7.4 at room temperature. The dialysis buffer was a 20 mM citrate and 15 mM glycine buffer, with a pH of 7.3 at room temperature. The concentration of HEPES was reduced from greater than 15 mM in the feed to less than 1 mM in the retentate.

TABLE 2

Data for Experiments 1-1, 1-2, 1-3, and 1-4

|  | Experiment 1-1 | Experiment 1-2 | Experiment 1-3 | Experiment 1-4 |
| --- | --- | --- | --- | --- |
| Feed volume (L) | 1.4 | 1.94 | 2.36 | 4.85 |
| Retentate volume (mL) | 330 | 235 | 410 | 1057 |
| Total filtrate volume (L) | 15.3 | 10 | 12.86 | 12 |
| Dialysis buffer volume (L) | 14.2 | 8.3 | 10.9 | 8.2 |
| Feed flow (mL/min) | 50 to 100 | 50 to 200 | 200 | 200 |
| TMP (mmHg) | −6 to 28 | 0 to 60 | −1 to 75 | n/a |
| Process time (min) | 152 | 123 | 143 | 207 |
| vWF protein yield (%) | 84.8 | 69 | 80.7 | 74.1 |
| Activity yield - vWF Ristocetin cofactor (%) | 80 | 74.9 | 105.8 | 73.4 |

Example 2

Two experiments were performed with vWF as the shear sensitive biopolymer with a hollow fiber dialysis module. The hollow fiber dialysis module had a 7000 cm$^2$ membrane surface area, a 30 micrometer thick membrane, a fiber length of 100 millimeters, and a fiber inner diameter of 200 micrometers. The membrane material was polyethersulfone. The experiments were performed at a feed flow rate of 300 ml/min with an initial volume reduction rate of 2 L/hr and a dialysis rate of 5 L/hr. The shear rate imparted by the feed flow rate was approximately 571 sec$^{-1}$. The concentrations of the feed streams were about 0.18 g vWF/L and about 0.22 g vWF/L. The concentrations of the retentate were about 0.88 g vWF/L and about 0.95 g vWF/L, respectively.

The solution buffer, in the feed stream, was a 20 mM HEPES and 150 mM NaCl buffer, with a pH of 7.4 at room temperature. The dialysis buffer was a salt free, 20 mM citrate and 15 mM glycine buffer, with a pH of 7.3 at room temperature. The concentration of HEPES was reduced from greater than 15 mM in the feed to less than 1 mM in the retentate.

TABLE 3

Data for Experiments 2-1 and 2-2

|  | Experiment 2-1 | Experiment 2-2 |
| --- | --- | --- |
| Feed Volume (L) | 10.5 | 12.7 |
| vWF total protein in feed (g) | 1.9 | 2.8 |
| Feed flow rate (mL/min) | 300 | 300 |
| TMP (mmHg) | 8 to 131 | −4 to 116 |
| Volume reduction rate (mL/h) | 2000 | 2000 |
| Dialysis rate (mL/h) | 5000 | 4000 |
| Total time (h) | 8.9 | 6.3 |
| vWF protein yield (%) | 108.5 | 79.6 |
| Activity - vWF Ristocetin cofactor yield (%) | 97.6 | 77.7 |

Figure 4:
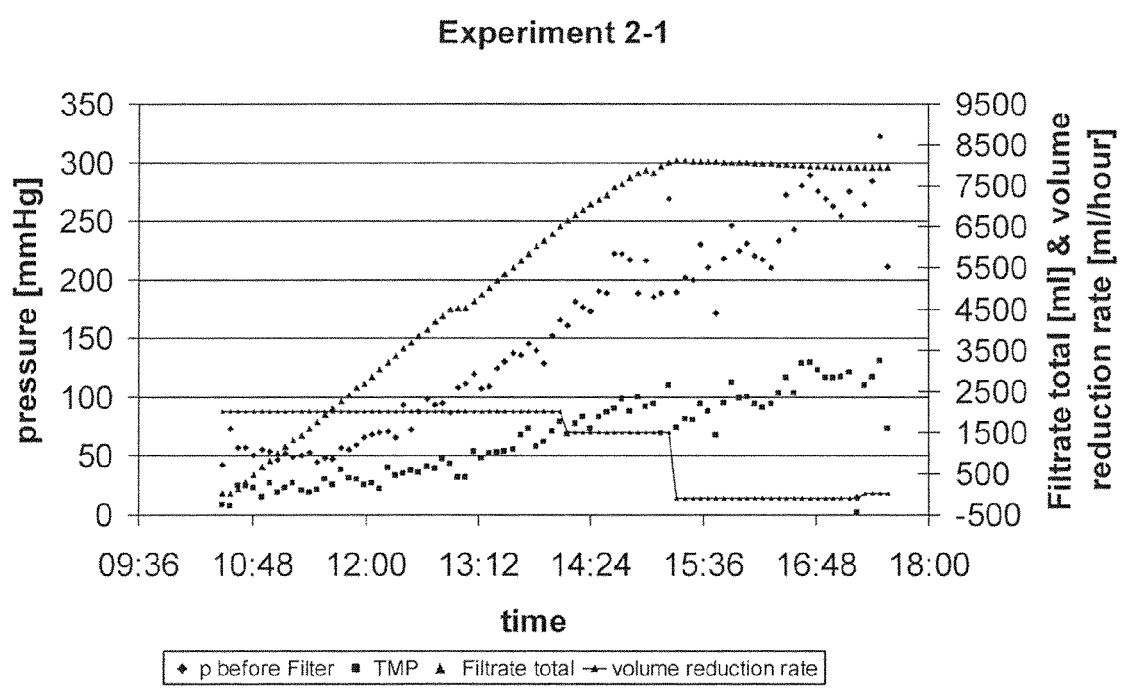

FIG. 4 is a graphical representation of Experiment 2-1 with data for transmembrane pressure, pressure before the filter, volume reduction rate, and total filtrate volume.

Comparative Example

Nine experiments were run on tangential flow hollow fiber devices, with a 300 kDa membrane, commercially available from GE Healthcare (Buckinghamshire, United Kingdom). The inner diameter of the tangential flow hollow fiber device was 0.5 mm. Six of the experiments were performed on tangential flow hollow fiber devices with a membrane surface area of 140 cm$^2$, and three were performed with a membrane surface area of 650 cm$^2$. The concentration process included an ultrafiltration step and a diafiltration step. The recommended shear rate for shear sensitive feed stock was 2000 to 4000 sec$^{-1}$, however these shear rates were too high for the shear sensitive biopolymer tested, vWF. Therefore, the experiments were run at lower flow rates than recommended to decrease the shear stress imparted to the biopolymers. After ultrafiltration, the average vWF protein yield was 50.7% and the vWF Ristocetin cofactor yield was 59.0%. After diafiltration, the final process, the average vWF protein yield was 48.3% and the vWF Ristocetin cofactor yield was 53.8%.

These yields were well below those achieved with the hollow fiber dialysis modules. In addition, the lower flow rates necessary to reduce the shear rates in the tangential flow hollow fiber devices increased process time to a prohibitive level. Without compensating for the resulting low filtrate flux associated with low flow rates, the process time is not economically feasible. The methods of increasing filtrate flux, such as increasing TMP or membrane surface area, result in losses of shear sensitive biopolymers to protein precipitation or surface adsorption.

The preceding examples demonstrate an effective method for concentrating shear sensitive biopolymers that achieves high yields by reducing shear stress and retaining a sufficiently high filtrate flux. This method ensures that the mixture containing shear sensitive biopolymers is concentrated without losing significant quantities of the biopolymer to structural transformation, protein precipitation, membrane fouling, and/or membrane surface adsorption.

The foregoing description is given for clearness of understanding only, and no unnecessary limitations should be understood therefrom, as modifications within the scope of the invention may be apparent to those having ordinary skill in the art.

What is claimed is:

1. A method for concentrating shear sensitive biopolymers, the method comprising flowing a mixture comprising a shear sensitive biopolymer and a solution buffer into a hollow fiber dialysis module to form a retentate, said retentate having a shear sensitive biopolymer concentration that is greater than that of the mixture, and a filtrate, wherein a transmembrane pressure between the mixture and the filtrate is about 1 mmHg to about 150 mmHg, wherein a membrane thickness of the hollow fiber dialysis module is less than about 200 micrometers, and wherein a wall shear rate in the hollow fiber dialysis module is less than about 2300 sec$^{-1}$ wherein the shear sensitive biopolymer present in the retentate retains an activity of at least 70% of the activity of the sensitive biopolymer present in the mixture.

2. The method of claim 1, wherein the membrane thickness of the hollow fiber dialysis module is about 10 micrometers to about 100 micrometers.

3. The method of claim 1, wherein the membrane thickness of the hollow fiber dialysis module is about 30 micrometers.

4. The method of claim 1, wherein the wall shear rate in the hollow fiber dialysis module is about 50 sec−1 to about 1800 sec−1.

5. The method of claim 1, wherein a membrane of the hollow fiber dialysis module comprises a material having protein adsorption below 1 gram per square meter.

6. The method of claim 1, wherein a membrane of the hollow fiber dialysis module comprises a material selected from the group consisting of polysulfone, polyethersulfone, polyvinylidene fluoride, polyimide, ceramic, modified cellulose, aliphatic polyamide, and polyacrylonitrile.

7. The method of claim 1, wherein a membrane of the hollow fiber dialysis module comprises a material selected from the group consisting of polysulfone, polyethersulfone, and modified cellulose.

8. The method of claim 1 further comprising displacing a portion of the solution buffer with a dialysis buffer.

9. The method of claim 1, wherein the retentate comprises at least about 70% of the shear sensitive biopolymer present in the mixture.

10. The method of claim 1, wherein the retentate comprises at least about 80% of the shear sensitive biopolymer present in the mixture.

11. The method of claim 1, wherein the retentate comprises at least about 90% of the shear sensitive biopolymer present in the mixture.

12. The method of claim 1, wherein the shear sensitive biopolymer comprises von Willebrand factor.

13. The method of claim 1, wherein the shear sensitive biopolymer present in the retentate retains an activity of at least about 80% of the activity of the shear sensitive biopolymer present in the mixture.

* * * * *